United States Patent [19]

Lincoln et al.

[11] Patent Number: 4,699,271
[45] Date of Patent: Oct. 13, 1987

[54] PLASTIC DISPENSING PACK FOR SURGICAL SUTURES

[76] Inventors: Jay P. Lincoln, 4839 E. Mt. Pleasant; William M. Owens, R.R. #3, Box 24; Douglas M. Ferguson, R.R. #1, Box 1020, all of Flagstaff, Ariz. 86001

[21] Appl. No.: 761,854

[22] Filed: Sep. 9, 1985

Related U.S. Application Data

[63] Continuation of Ser. No. 620,413, Jun. 14, 1984.

[51] Int. Cl.⁴ ............................................. A61B 17/06
[52] U.S. Cl. .................................... 206/63.3; 206/380
[58] Field of Search .................... 206/63.3, 380, 227, 206/382, 381

[56] References Cited

U.S. PATENT DOCUMENTS

| | | | |
|---|---|---|---|
| 3,280,971 | 10/1966 | Regan et al. | 206/63.3 |
| 3,338,401 | 8/1967 | Regan, Jr. | 206/63.3 |
| 3,972,418 | 8/1976 | Scholer et al. | 206/63.3 |
| 4,391,365 | 7/1983 | Batchelor | 206/63.3 |
| 4,424,898 | 1/1984 | Thyen et al. | 206/63.3 |

FOREIGN PATENT DOCUMENTS 2754936  6/1978  Fed. Rep. of Germany ..... 206/63.3

*Primary Examiner*—Joseph Man-Fu Moy

[57] ABSTRACT

An improved package for needled sutures comprising a plastic pack for one or more PTFE (optionally silk, cotton or other) sutures sealed within protective plastic envelopes wherein the suture is arranged within molded compartments of the pack, spaced apart by thin plastic spacers where multiple sutures are housed, and the needles firmly held across a U-shaped slot at the top of the holder by tabs or in curved slots so as to be easily accessible from either side of the pack when the protective envelopes are opened.

15 Claims, 11 Drawing Figures

PLASTIC DISPENSING PACK FOR SURGICAL SUTURES

This is a continuation of application Ser. No. 620,413 filed June 14, 1984.

This application is related to application Ser. No. 620,605, titled *Multi-Panel Folder For Surgical Sutures*, by Douglas M. Ferguson, William M. Owens, Michael F. Lang, and Jay P. Lincoln, filed or even date to this application.

BACKGROUND OF THE INVENTION

1. Technical Field

This invention relates to packages for surgical sutures, and more particularly to folded, molded or vacuum-drawn plastic dispensers for certain kinds of sutures having needles attached hereto.

2. Background Art

Packages for surgical sutures having needles attached at one or both ends are constructed according to the nature of the suture material and to how the sutures will be used. Generally, the package holds the suture and attached needles in place, protects them during handling and storage, and allows ready access to the suture for removal with minimum handling at the time the suture is to be used. The suture should also be removable without becoming entangled with itself, kinked or coiled in undesired ways. The nature of the suture material itself may impose limitations on the configuration of the package, how the suture is placed within the package, the placement of the needles, or how the suture is drawn from the package.

A frequently used form of package consists of a folded stiff treated paper suture holder contained in a sterile, hermetically sealed envelope, which envelope is further sealed in a second, usually clear, thermoplastic heat-sealed envelope outer wrap to maintain the suture holder and inner envelope sterile. When the suture is to be used, the outer clear wrap is opened in the operating room and the sealed sterile inner envelope deposited in a sterile area. Sterile personnel then open the inner envelope when access to the suture is needed. A number of these direct dispensing packages represent great advances in the art of surgical suture packaging, but many of them do not address the problems associated with the peculiar properties of sutures manufactured from porous expanded polytetrafluoroethylene (PTFE), which has been prepared in accordance with one or more U.S. Pat. Nos. 4,187,390; 4,110,392; 4,096,227; 3,962,153 and 3,653,566. Many of the prior packages are not suitable in that crimping, flattening, tangling, or knotting may occur during loading, handling, or removing a PTFE suture from the package. Cuts and slots or other breaks in the surface smoothness in the suture holding area of the paper holder associated with loading or holding a suture-tend to damage a PTFE suture drawn across the cut edge. It has been found that mechanically loading a PTFE suture in a package by winding the suture about mandrels or reels in a figure eight or a circular configuration tends to induce tangling or knotting of the suture upon removing it from the package. Any loading pattern in which the PTFE suture intersects itself can lead to knotting. Friction pads, such as those made from polymer foam, used to hold a suture in place, also tend to induce tangling and knotting. Cotton and silk sutures have also been found to sometimes tangle or knot under the same circumstances as PTFE sutures and hence the suture holder of this invention can be usefully employed for sutures manufactured from cotton or silk, or other pliable suitable material. Additionally, although many suture packages attempt to fix any attached needles in a particular location for easy presentation to the user, it has been found that often the needles become dislodged and are not conveniently presented to the user. If the needles do remain fixed in place, they are often accessible from one direction only.

Reel windup suture holders molded from plastic, such as those disclosed by U.S. Pat. Nos. 3,545,608, 3,648,949, and 4,084,692, have advantages for many sutures. PTFE sutures will, however, generally quickly tangle or knot when withdrawn from these or similar types of reels. Coiled narrow passageways molded in plastic are shown by U.S. Pat. Nos. 3,338,401 and 3,972,418, wherein several sutures lie side by side along the passageway. These also are not suitable in that PTFE sutures may generally not be drawn past one another along their length without entanglement and knotting.

Thus, the plastic suture dispensing pack of this invention has several advantages over prior art packages for PTFE sutures. The advantage of non-overlapping or PTFE suture strands is combined with holding of the needles in a fixed position in a unique orientation which presents the needles in such a way that they may be gripped from either side of the package by a needle holder. Right-handed or left-handed removal of the needle and suture is equally facile. The needles are immediately visible in a slot in the top of the suture folder on only a partial peeling back of the inner protective envelope and can be immediately gripped in the slit from either side of the pack and the suture easily withdrawn from the pack without further opening of the protective envelope.

SUMMARY OF THE INVENTION

The present invention is characterized by a 2-part folded, molded plastic dispensing pack for a suture with one or two attached needles which is sealed in an inner protective envelope and an outlet clear protective envelope. The plastic suture pack has a first panel connected by molded plastic hinges along a major edge to a second panel along a portion of a major edge. Both panels and the connecting hinges are molded simultaneously as one piece. The first panel is flat and has linear access slots extending across the width of the panel disposed at even predetermined distances apart down its length with holes spaced in between the slots so as to receive and hold the tops of the ends of dividers which form suture holding compartments in the second panel.

The second panel is longer than the first panel, the needle-holding portion extending above the first panel, has chamfered upper corners to ease insertion of the loaded folded pack into a protective envelope, an optional suture retainer slot cut into the left end of the upper edge, a U-shaped notch disposed in the center of the upper edge, two plastic needle clips or holders disposed one on each side of the U-shaped notch, and evenly disposed below the U-shaped notch and needle clips, a series of interconnected separate molded suture compartments arranged on an even predetermined spacing in registration with the slots of the first panel when the first panel is folded over the second panel. The dividers between the suture compartments end in integrally molded slightly tapered pins (optionally at both ends) which extend above the surface of the second panel so as to penetrate the holes provided in the first panel or closure of the pack to hold the first panel firmly to the face of the second panel by tight pressure fit in the holes.

An alternative form of second panel which may be used, utilizes matched pairs of curved slots cut into the sides of the U-shaped notch, slots curved to fit and hold in place across the notch one or two needles in each pair of slots. Several pairs of such curved slots are used where more than one suture is to be loaded into the pack. If the pack is to be multiply loaded, a very thin, smooth plastic spacer which fits within and has the same shape as the molded suture compartment is inserted between each suture to prevent its touching its neighboring suture with the results described above.

Another alternative form of second panel may be used which can utilize either the plastic needle clips or the matched pairs of slots to hold surgical needles across the U-shaped access notch, but has linear access slots cut or molded into the bottom of each molded suture compartment. Where this option is utilized, an alternative first panel is used with it which embodies only holes spaced at predetermined distances apart down its length to receive and hold the tops of the ends of the dividers which form suture holding compartments in the second panel.

Where pins or pegs are molded onto both ends of the suture compartment dividers of the second panel to fit into corresponding holes in the first panel to hold the two panels firmly interlocked as a unitary dispensing pack, the first panel has two rows of spaced holes to accommodate those pins when the first panel is folded over onto the second panel. In this option, the interlocking tongue and groove molded into the edges of the two panels need not be used. Either the plastic needle clips or the molded slots may be used to hold the surgical needles across the U-shaped needle access notch with these panel options. It can thus be seen that the various options for holding the surgical needles in place, for holding the suture-enclosing panels together, and for providing access slots to the suture compartments can be selected and sized as appropriate for the kinds and sizes of sutures and needles being dispensed from the pack.

On loading, the needles attached to the suture are fixed in place across the U-shaped notch of the second panel behind the clips or in a set of slots in the alternative pack, the suture disposed along the space provided along the intreconnection channel of the suture compartment, the first panel folded over to cover the suture compartment of the second panel and affixed in place by interlocking tongue and groove or other suitable means molded into the edges of the two panels, as well as or alternatively the pins of the second panel fitting the holes in register with them on the first panel, and the suture disposed in sinusoidal configuration in the suture compartments with utilization of the access slots of the first panel. In both alternative needle holding embodiments, the needle point always faces to the right, away from the suture channel into the suture holding compartments, the needles are firmly held in place across the U-shaped slot by either the plastic clips or the needle slots such that the needles are readily available for either left-hand or right-hand removal. The PTFE, or optionally, the silk or cotton or other suitable suture for which the pack is intended, lies in a sinusoidal configuration with no element of suture touching any other element of suture to avoid tangling or knotting on removing the suture from the pack. The plastic pack of this invention can also be used with sutures other than those for which its design is particularly and specifically intended.

Other and further advantages of this invention will appear to one skilled in the art from the following description and claims together with the drawings.

Description Of The Preferred Embodiments

Figure 1:
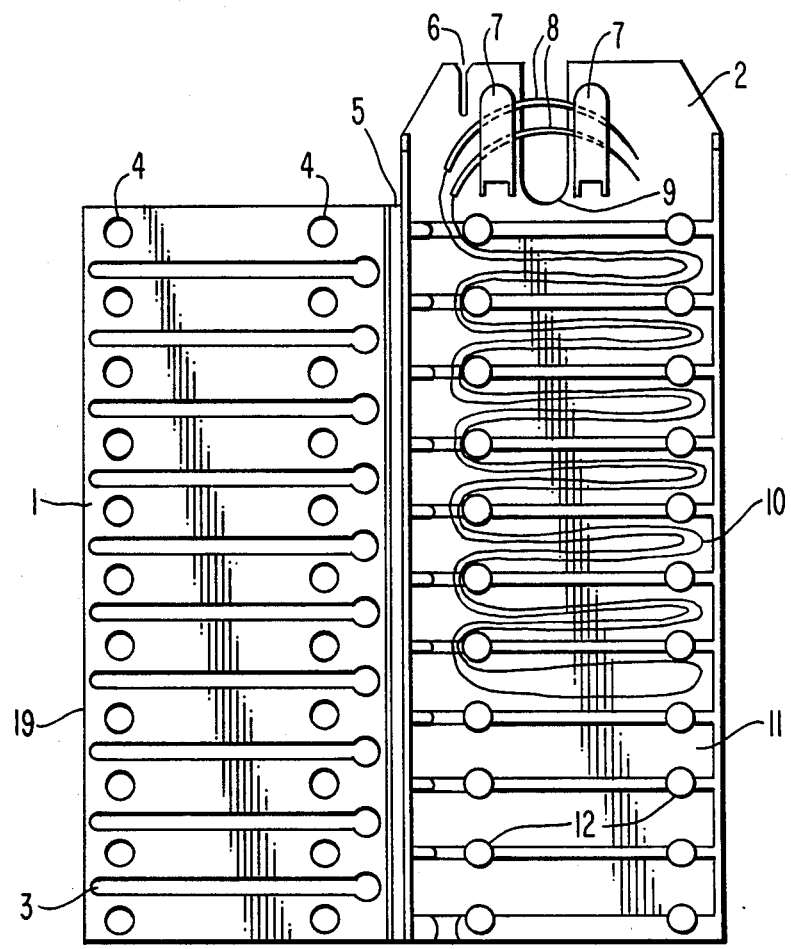
FIG. 1 is a front plan view of the unfolded plastic pack of the invention shown containing a suture with a needle attached at each end, both needles held in place behind the clips on either side of the U-shaped notch.

Referring now to the drawings, identical numerals are used for identical parts in each of the figures to aid in the description of the suture pack of the invention. FIG. 1 shows in unfolded configuration (as it was molded) the two panel plastic pack of the invention. The first panel 1 is joined by integrally molded plastic hinges 5 to a second panel 2 and when folded over onto panel 2 covers the suture holding compartment but not the needles 8 and the clips 7 holding them across U-shaped notch 9. The fist panel 1 has a series of spaced slots 3 extending across its width at predetermined spacings with holes 4 disposed between the slots 3. Slots 3 are thruslots, through panel 1. The holes 4 are in register with the register with the molded ends 12 of the dividers between the suture holding compartments 11 so that a tight pressure fit is obtained when the pack is closed and the two panels are held firmly together. Ends 12 are slightly tapered to assure firm holding.

The second panel 2 has an edge slot 6 which may optionally be utilized to anchor the end of a suture, a U-shaped notch 9 across which molded plastic clips 7 firmly hold in place needles 8 which are attached to suture 10. Clips 7 may be punched out from the body of panel 2 or optionally molded in place as panel 2 is being molded. Suture 10 is shown disposed in a sinusoidal configuration as provided by the shape of the suture holding compartments 11. The ends 12 of the separators between suture holding compartments 11 are molded to extend above the surface of the remainder of panel 2 and extend slightly above the outer surface of panel 1 when in closed position covering a portion of the face of panel 2. Ends 12 are tapered as well, so as to aid in locking them firmly in place in holes 4.

Figure 1A:
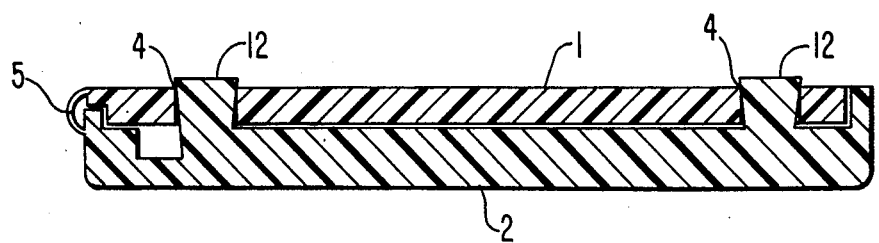
FIG. 1A shows a cross-sectional view of the pack cut through one divider between compartments. The pack is shown closed and locked.

FIG. 1A shows a cross-sectional view of the pack cut through across the pack at the level of one of the dividers between suture compartments 11. Panel 1 is folded over onto panel 2 to form a closed and locked pack, Panel 1 is shown optionally hinged 5 to panel 2, molded ends 12 of a compartment divider are held by their taper in holes 4 of panel 1.

Figure 1B:
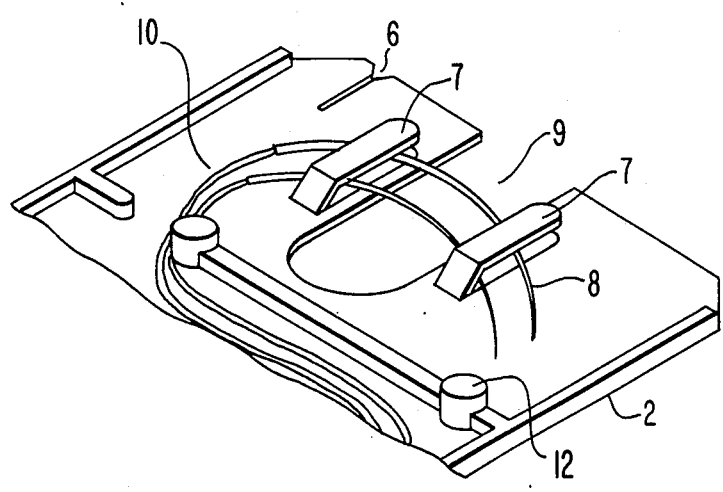
FIG. 1B is a broken perspective view of the top of panel 2 in which suture-bearing needles are shown held by integral plastic clips across the U-shaped notch 9 in the top edge of the panel.

The FIG. 1B broken perspective view of the top of panel 2 illustrates how a pair of needles 8 attached to a suture 10 are held by a pair of integral plastic clips 7 across slot 9 where they can be conveniently reached for easy removal from either side of slot 9 of the pack.

Figure 1C:
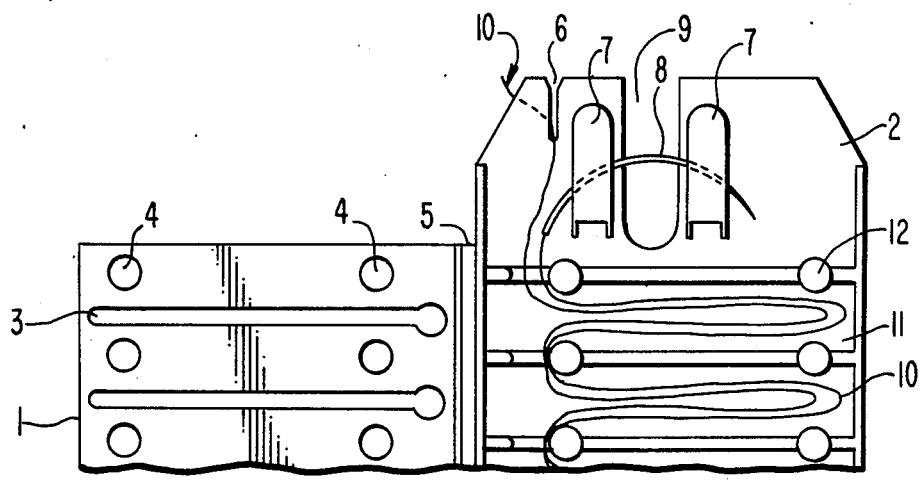
FIG. 1C is a broken view of the top of the pack with a single needle with suture held by plastic clips and the free end of the suture held in slot 6 in the top of panel 2.

FIG. 1C is a broken plan view of the pack wherein a suture 10 bearing a single needle 8 is alternatively held by its free end in slot 6.

Figure 1D:
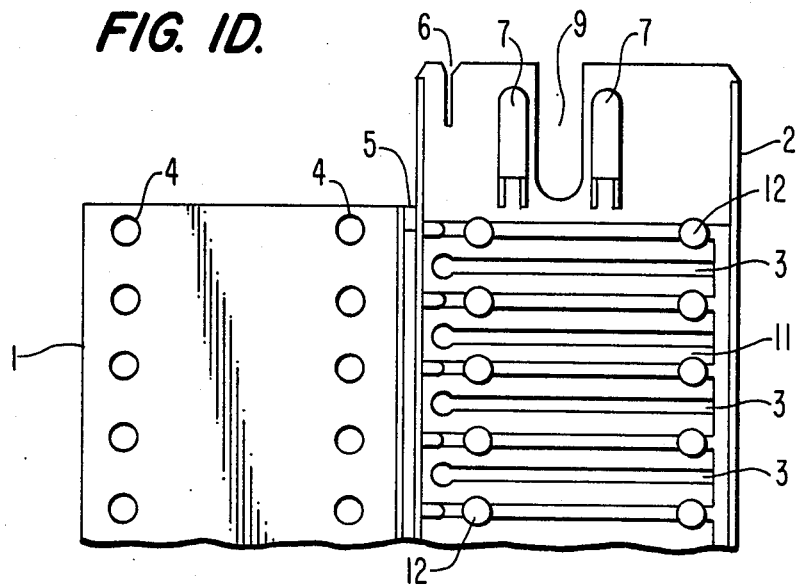
FIG. 1D is a broken plan view of the plastic pack to show access slots in the bottom of the suture compartments as an alternative to placing them in panel 1.

FIG. 1D depicts an alternative location for thru-slots 3. The broken view shows slots 3 disposed at the bottom of suture holding compartments 11 of panel 2 instead of in panel 1 between the sets of holes 4.

Figure 2:
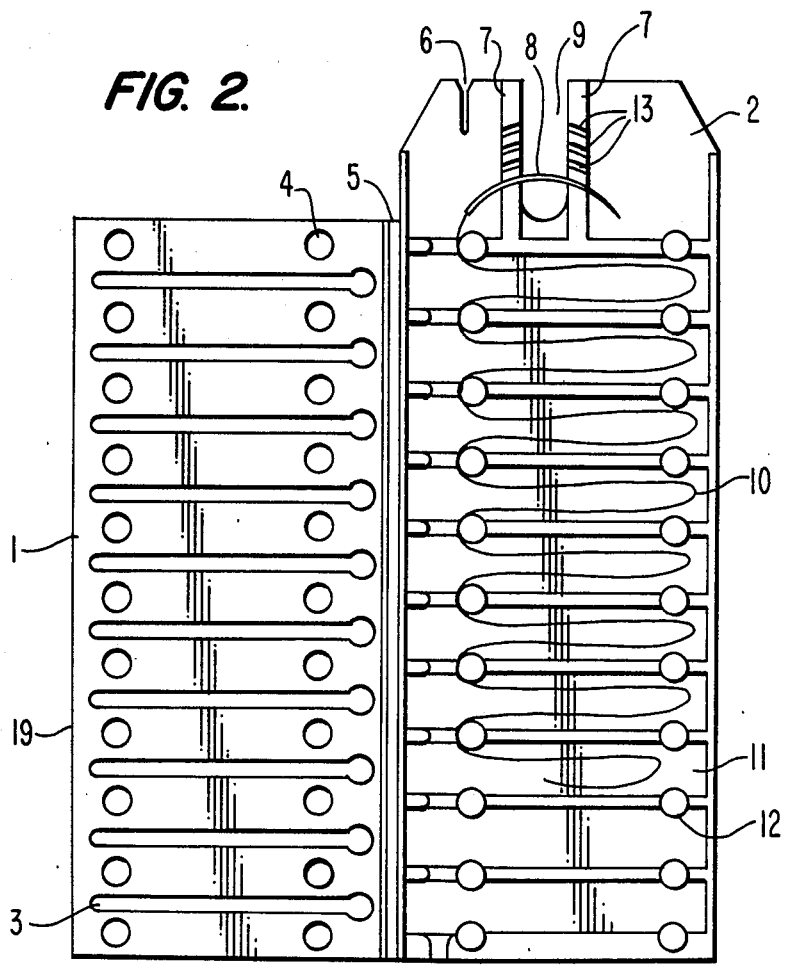
FIG. 2 is a plan view of the alternative embodiment of the invention showing a suture bearing one attached needle, the needle held in place in a pair of slots cut in the edges of the U-shaped notch.
Figure 2A:
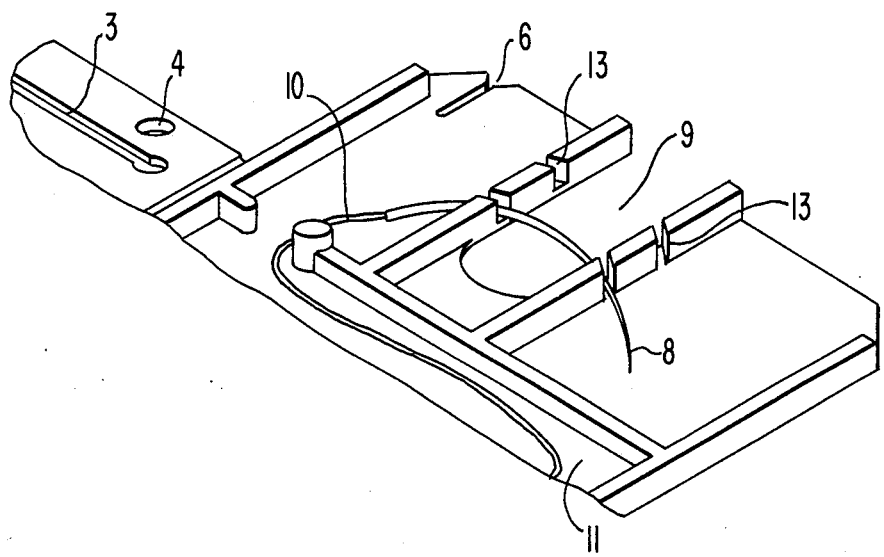
FIG. 2A is a broken perspective view of a needle held in a pair of slots across the U-shaped notch 9 in the top edge of panel 2.
Figure 3:
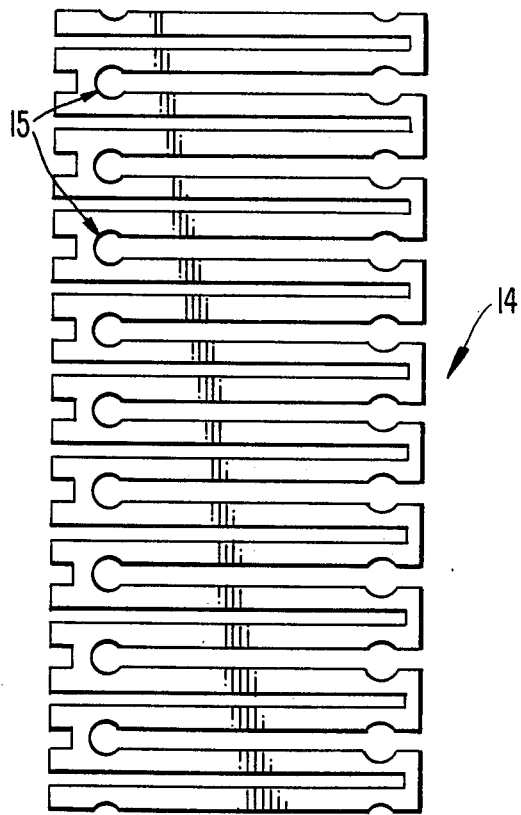
FIG. 3 is a plan diagram of a thin plastic separator which is disposed within the suture holding comprtment to separate sutures in a multiply-loaded pack.

FIG. 2 dsecribes another embodiment of the invention wherein pairs of shaped slots 13 extend in predetermined curves across U-shaped notch 9, curves chosen to match the curvature of the needles 8 to be placed in the pack. Where multiple sutures with attached needles are to be packaged, it is necessary in the case of PTFE sutures for which the packs of the invention are designed to be spaced apart from each other within the suture holding compartment 11 by thin plastic separators 14 as shown in FIG. 3. The separators 14 are held in place in compartment 11 by careful sizing and registration of round slot ends 15 with ends 12 of the compartment dividers.

Figure 3A:
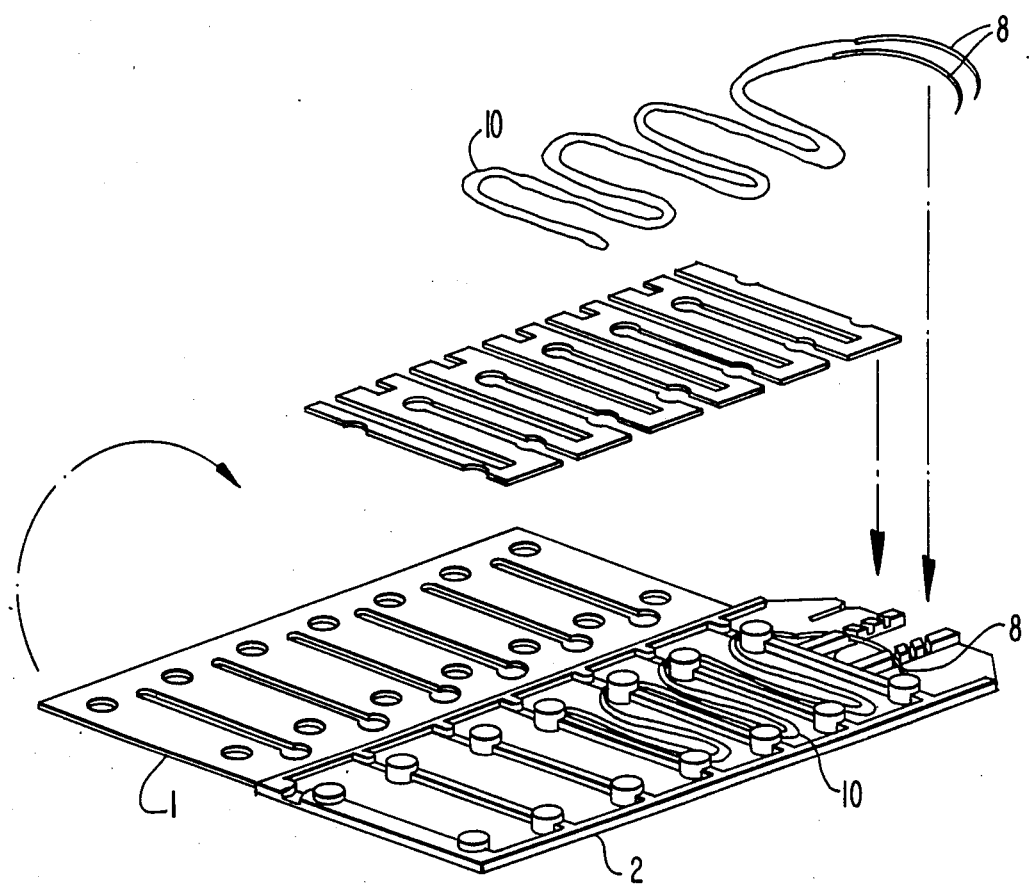
FIG. 3A is an exploded perspective view of the pack with one suture disposed within the compartment, one spacer to be placed on it, and another suture to be placed on the spacers.

FIG. 3A is an exploded perspective view of the option where molded curved slots are used to hold pairs of needles in place across the U-shaped slot. In this view, one suture 10 is shown loaded in the pack, a thin plastic divider above and between it, and the next suture to be loaded into the pack. The needles attached to this suture would be disposed in an open shaped slot above that depicted as holding those of the lower suture in place.

Figure 4:
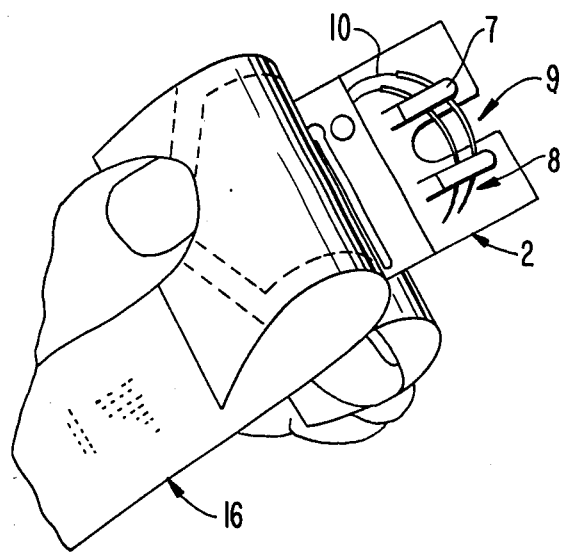
FIG. 4 shows a partially peeled back inner protective envelope with the suture pack displaying the needles in readily available position.

FIG. 4 depicts a pack of the invention with needles 8 exposed for ready use by grasping from either side of slot 9 in equally facile manner in a partially peeled back inner protective envelope 16. The needles 8 are completely visible either on the side of the pack on which they are held in place or through the transparent plastic of the corpus of the pack.

Figure 5:
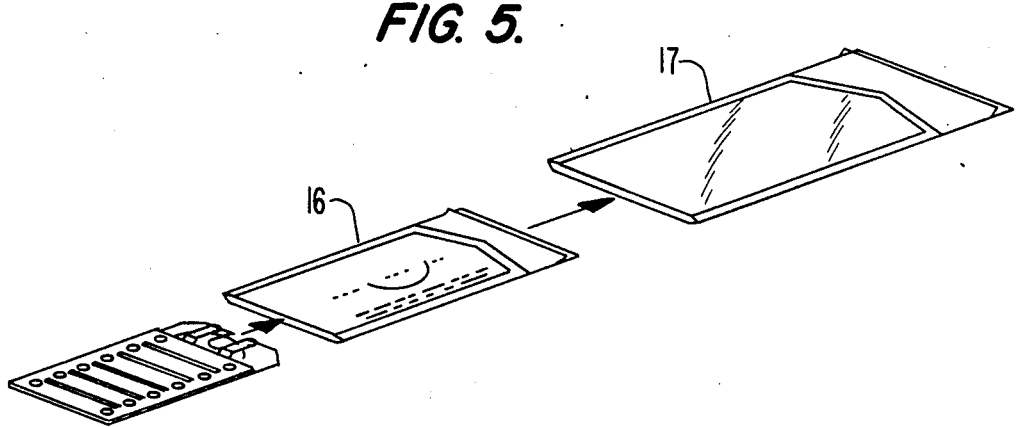
FIG. 5 shows how the plastic suture pack is inserted into an inner protective envelope which is sealed and in turn is inserted into the outer clear envelope which is also sealed.

FIG. 5 shows a suture and needle-loaded pack of the invention which is ready to be placed inside inner protective envelope 16. Envelope 16 is sealed, then inserted inside clear outer protective envelope 17, envelope 17 sealed, the packaged packs cartoned, and then sterilized with, for instance, ethylene oxide gas. Printed indicia regarding contents and instructions for use are usually disposed on the inner protective envelope 16.

The plastic suture pack may be manufactured from injection moldable plastics known in the art, such as polypropylene, polyethylene, polysulfone and other polymers. The suture dividers utilized with multiple suture loadings may be cut from plastic sheets or molded from common plastics such as those cited above. The inner and outer protective envelopes are usually of heat sealable thermoplastic polymers, such as, for instance, polyethylene, polypropylene, polyvinyl acetate-ethylene copolymer, or Tyvek (DuPont de Nemours trademark) diolefin polymer, which may also be in the form of composites with paper, aluminmum foil, or other appropriate materials. It is preferred that the inner envelope be a composite bearing any required printed indicia and that the outer envelope be of a clear heat-sealable thermoplastic material. The porous expanded polytetrafluoroethylene utilized as suture material is that listed above.

Having described the invention in detail and many of the ways it may be carried into practice, it will be apparent to those skilled in the art that many variations, modifications, and extensions of the basic principles embodied may be made without departing from the spirit or scope of the invention and that the foregoing exemplifications and descriptions are not intended to be limiting of the scope of the invention.

We claim:

1. A molded plastic dispensing pack for surgical sutures comprising:
   (a) a first panel closure means hingedly affixed to:
   (b) a second panel having integrally molded interconnected compartments for protectively holding said sutures, each of said compartments having an access slot for loading said sutures;
   (c) a pair of integrally molded plastic holders, one of each pair disposed on each side of a generally U-shaped slot formed in the top edge of said second panel, said holders shaped and located so as to hold surgical needles attached to each of said sutures firmly in place across said slot;
   (d) integrally molded means for interlocking said first and second panel portions of said pack in place upon closure, the dimensions of said panels being such that the means for holding said needles extends beyond said first panel upon closure; and
   (e) one or more divider sheets of contour approximately that of said suture holding compartments, each of said sheets disposed between any two sutures present in said compartment, where a plurality of sutures are loaded into said dispensing packs and the number of said divider sheets is one less than the number of sutures contained within said compartments.

2. A suture package comprising in combination a dispensing pack of claim 1 and a suture having attached at least one surgical needle.

3. A suture package of claim 2 wherein the suture contained therein has a needle affixed to each end.

4. A suture package of claim 1 wherein the suture is comprised of porous expanded polytetrafluoroethylene.

5. A suture package of claim 2 wherein the suture is comprised of porous expanded polytetrafluoroethylene.

6. A suture package of claim 1 which contains a suture which has been disposed mechanically therein.

7. A suture package of claim 1 wherein the access slot to each suture holding compartment is molded into the bottom of said compartment.

8. A suture package of claim 1 wherein access slots to said suture holding compartments are molded into the portion of said package which is folded over said compartment to close it.

9. A suture package of claim 1 wherein said interlocking means comprises a tongue and groove system integrally molded into the edges of said package.

10. A package of claim 1 wherein said interlocking means comprises shaped apertures situated in a predetermined pattern in portions of said package and when said package is folded together, said apertures fit over and interlock with integrally molded pins of similar shape located in registration with said apertures on other portions of said package.

11. A package of claim 10 wherein the shape of the apertures and pins is circular.

12. A suture package of claim 2 which has been sealed into one or more plastic protective envelopes and the sealed package sterilized.

13. A package of claim 1 wherein the plastic is injection-moldable.

14. A package of claim 1 wherein the plastic comprises polypropylene, polyethylene, polysulfone, polystyrene and copolymers of styrene, polyvinyl chloride, acrylonitrile-butadienestyrene polymers, acrylics, cellulosics, polyamide polymers, acetal, polycarbonate, fluoroolefin polymers, or silicone rubber.

15. A suture package of claim 1, wherein the suture contained therein has a needle affixed to each end.

* * * * *